United States Patent
Xu et al.

(10) Patent No.: US 7,986,988 B2
(45) Date of Patent: Jul. 26, 2011

(54) REFERENCE HEIGHT CALIBRATION SCHEME FOR MODULAR MULTI-MODALITY MEDICAL IMAGING SYSTEM

(75) Inventors: Ray S. Xu, Algonquin, IL (US); Robert Peter Hurley, III, Streamwood, IL (US); James T. Chapman, Glen Ellyn, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 444 days.

(21) Appl. No.: 12/240,787

(22) Filed: Sep. 29, 2008

(65) Prior Publication Data
US 2009/0088621 A1    Apr. 2, 2009

Related U.S. Application Data

(60) Provisional application No. 60/995,578, filed on Sep. 27, 2007, provisional application No. 60/995,576, filed on Sep. 27, 2007, provisional application No. 60/995,528, filed on Sep. 27, 2007.

(51) Int. Cl.
*A61B 5/055* (2006.01)
*A47B 13/00* (2006.01)
*A61G 7/00* (2006.01)
*H05G 1/60* (2006.01)

(52) U.S. Cl. ........ 600/415; 600/436; 600/407; 600/425; 5/630; 5/647; 378/4

(58) Field of Classification Search ....................... None
See application file for complete search history.

(56) References Cited

U.S. PATENT DOCUMENTS

| | | | | |
|---|---|---|---|---|
| 5,105,086 A | * | 4/1992 | Pierfitte et al. | 250/363.08 |
| 5,490,296 A | * | 2/1996 | Fleury et al. | 5/601 |
| 5,960,054 A | * | 9/1999 | Freeman et al. | 378/4 |
| 6,574,808 B1 | * | 6/2003 | Brown et al. | 5/601 |
| 2003/0230723 A1 | * | 12/2003 | Garrard et al. | 250/363.1 |

* cited by examiner

*Primary Examiner* — Unsu Jung
*Assistant Examiner* — Lawrence N Laryea
(74) *Attorney, Agent, or Firm* — Peter L. Kendall

(57) ABSTRACT

A reference height calibration procedure obtains a reference error value, which can be used to adjust a height calibration parameter for registering the fields of view (FOVs) of the modules of a multi-modality medical imaging system such as a SPECT-CT imaging system.

7 Claims, 3 Drawing Sheets

REFERENCE HEIGHT CALIBRATION SCHEME FOR MODULAR MULTI-MODALITY MEDICAL IMAGING SYSTEM

CROSS-REFERENCE TO RELATED APPLICATIONS

This application claims benefit under 35 U.S.C. §119(e) to:
U.S. Provisional Patent Application Ser. No. 60/995,528 filed on Sep. 27, 2007;
U.S. Provisional Patent Application Ser. No. 60/995,576 filed on Sep. 27, 2007; and
U.S. Provisional Patent Application Ser. No. 60/995,578 filed on Sep. 27, 2007,
which are hereby incorporated by reference in their entireties.

BACKGROUND OF THE INVENTION

1. Field of the Invention

The invention relates to accurately registering field of views (FOVs) for loosely-coupled modular multi-modality imaging systems, such as cardiac SPECT-CT systems that share the same patient table, but do not have any common installation platform.

2. Description of the Related Art

In modular multi-modality medical imaging systems, wherein modules may be added and combined in a flexible manner, the modules are loosely integrated in that they do not share any common installation platform. In order to make use of multi-modality imaging, the modules must be co-registered with respect to their FOVs so that the images produced by the separate modules can be fused or combined into a composite image for clinical analysis.

In such system, the gantry heights, and thus the centers of rotation of, for example, a single photon emission computed tomography (SPECT) module and a computed tomography (CT) module are individually adjustable, typically within a range of from about −10 mm to about +15 mm. Floor unevenness can also cause a misalignment of ±½ inches between the modules. Additionally, other uncorrelated mechanical and/or installation errors can cause misalignments in heights between the modules. The maximal error in determining a center of reference line for a modular NM imaging system can be over 2 inches. This error is larger than the tolerance of SPECT module on a table height of ±2 mm. Moreover, if the error is not calibrated, the misalignment will result in either a collision in a TOMO scan, or part of the phantom image out of the field of view (FOV). In either case, a FOV calibration procedure fails.

For the foregoing reasons, there is a need for a device and method providing reference height calibration to allow for FOV calibration in a loosely coupled multi-modality modular medical imaging system.

BRIEF SUMMARY OF THE INVENTION

The present invention solves the existing problem in the art by providing a reference height calibration procedure that obtains a reference error value, which can be used to adjust a height calibration parameter for registering the fields of view (FOVs) of the modules of a multi-modality medical imaging system such as a SPECT-CT imaging system.

The reference height calibration procedure images a point source of radiation at a known location with respect to a known height position of a patient bed using an imaging module of a first modality, and measures the distance of the point source from a center of the FOV of the imaging module. This distance is then compared with a design height of the system as designed for the second imaging module, and a reference error value is obtained to compensate for the difference between the measured height and the design height of the patient bed.

BRIEF DESCRIPTION OF THE DRAWINGS

These and other features, aspects, and advantages of the present invention will become better understood with reference to the following description and appended claims, and accompanying drawings where:

DETAILED DESCRIPTION OF THE INVENTION

The present invention may be understood more readily by reference to the following detailed description of preferred embodiments of the invention as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Various embodiments of the present invention relate to a reference height calibration (RHC) procedure, which is preferably performed at the installation of a modular multi-modality medical imaging system.

It has been surprisingly discovered that the calibration procedure according to various embodiments of the present invention addresses the problems associated with the gantry height registration between CT and other modular nuclear medicine (NM) subsystems in a system comprising loosely integrated modules where there is no designed common platform for installation.

In such modular NM imaging systems the limitations in the motion architecture of components of the modular multi-modality medical imaging system impose a tight tolerance on the patient bed height during NM scans. Typically, the bed height tolerance is ±2 mm during NM scans. Additionally, the image co-registration subsystem in modular imaging systems according to the present invention, require a common reference line between CT and other modular NM subsystems and/or components. The accuracy in locating such a line directly translates to the accuracy in the initial CT-NM image registration.

Preferably, intrinsic co-registration is achieved as described in U.S. Provisional Patent Application Ser. No. 60/995,528 filed on Sep. 27, 2007, which is hereby incorporated by reference in its entirety. These requirements cannot be met by design due to the uncorrelated mechanical and/or installation errors, and primarily, the unevenness of the floor surface on which each module is installed. The floor surface unevenness is typically much more than 2 mm.

According to various embodiments of the present invention, the height registration between the bed or multiple purpose table (MPT) and the CT detector is preferably assured either by design or via a calibration procedure performed at the installation prior to the reference height calibration procedure according to the present invention, and therefore the bed and the CT detector are treated as one system. It is also preferable to assume that the modules are leveled within specifications.

Figure 1:
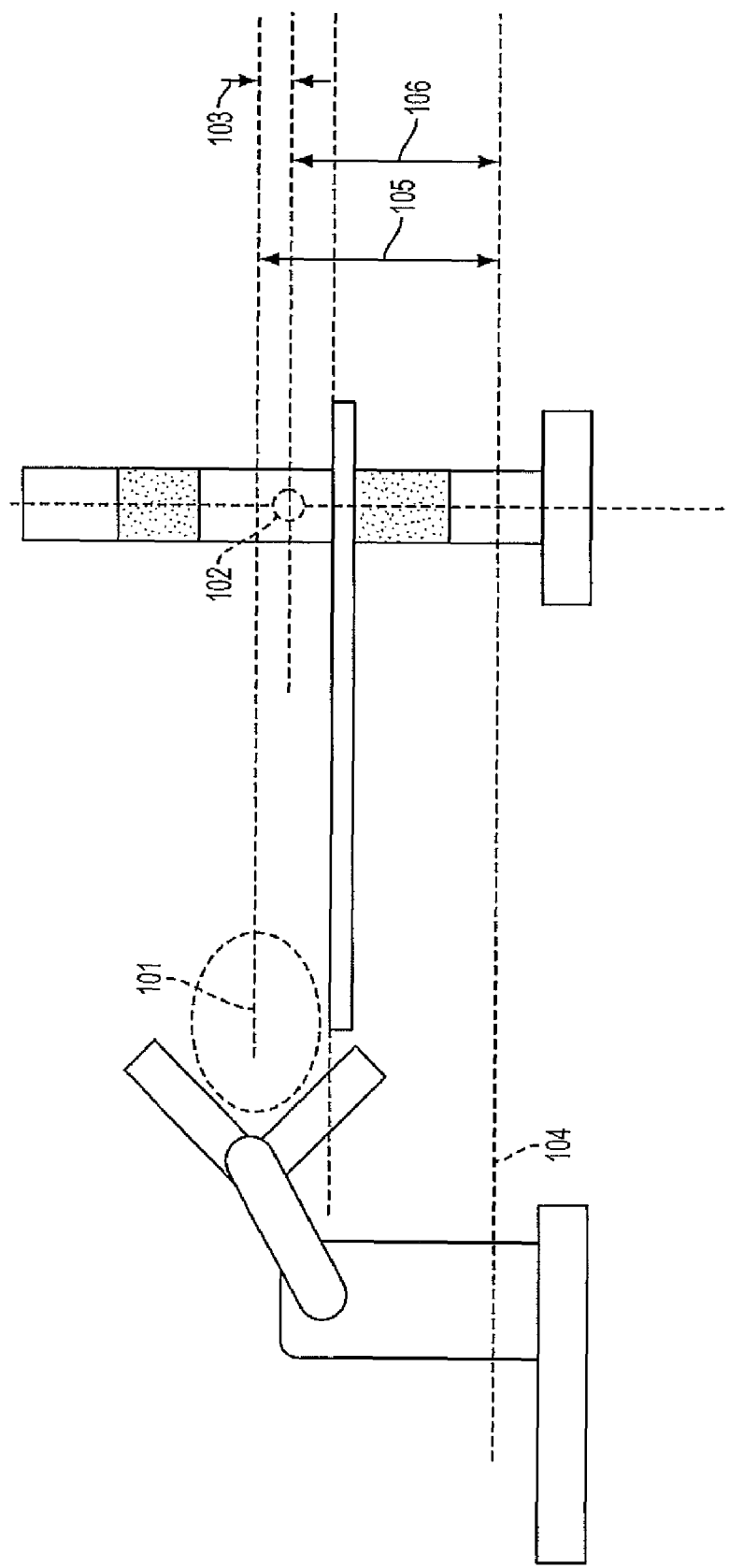
FIG. 1: shows an example modular multi-modality imaging system of a type applicable to the present invention, illustrating how $Y_{NMCenter}$ can be derived from a common reference line.

As shown in FIG. 1, the difference in height between a center of rotation of a gamma camera orbit (101) and a CT center of rotation (102) gives a parameter called $Y_{NMCenter}$ (103), a critical parameter in calculating Y position for DICOM conformed NM images. $Y_{NMCenter}$ (103) is preferably derived given a common reference line (104) for the gamma camera and CT devices. The height of the center of rotation of gamma camera orbit (101) from the common reference line (104) is $Y_{gamma}$ (105). The height of the center of rotation of the CT scanner (102) is $Y_{ct}$ (106). $Y_{NMCenter}$ (103) is thus the difference between $Y_{gamma}$ (105) and $Y_{ct}$ (106).

Figure 2:
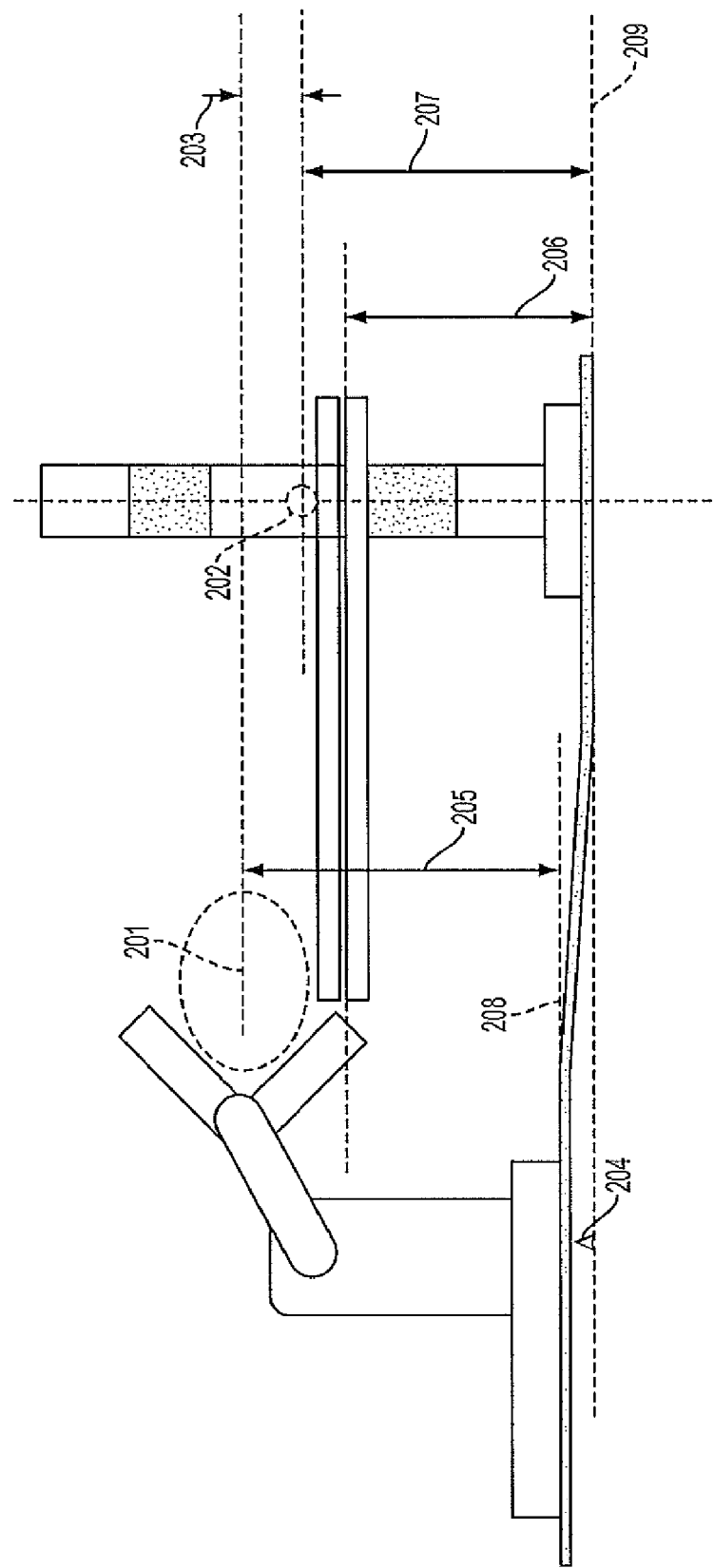
FIG. 2: shows an example modular multi-modality imaging system of a type applicable to the present invention, illustrating how a reference error can be caused by an uneven floor.

FIG. 2 illustrates the difference in height between a center of rotation of gamma camera orbit (201) and a CT center of rotation (202) when the gamma camera and CT detector modules are installed on an uneven floor. The height difference is denoted as $Y_{NMCenter}$ (203), a critical parameter in calculating Y position for DICOM conformed NM images. Here, $Y_{NMCenter}$ (203) cannot be derived from a common reference line due to the reference error of Δ (204). The aggregated effect of an uneven floor, mechanical, and installation errors may be assumed to result in reference error of Δ (204), i.e. the height difference between the bottoms of the two modules, as measured by module reference lines (208) and (209).

The height of the center of rotation of gamma camera orbit (201) from module reference line (208) (base of gamma camera) is $Y_{gamma}$ (205). The height of the center of rotation of the CT scanner (202) from reference line (209) at the base of the CT scanner is $Y_{ct}$ (207). The design height of the patient bed from reference line (209) at the base of the CT scanner is $Y_{NMScan}$ (206). Here, $Y_{NMCenter}$ (203) is preferably derived from Equation 1:

$$YNMCenter = YCT - Ygamma - \Delta \quad 1.$$

As shown in FIG. 2, due to the floor unevenness, the patient bed must be raised by Δ from the design scan position $Y_{NMScan}$ in order to obtain a reliable $Y_{NMCenter}$.

It has been surprisingly discovered by the present inventors that the reference error Δ is reliably and efficiently determined and accounted for, according to the reference height calibration of various embodiments of the present invention. The reference height calibration is preferably performed at the installation, but before the standard center of rotation (COR) calibration and the field of view (FOV) calibration as described in U.S. Provisional Patent Application Ser. No. 60/995,576 filed on Sep. 27, 2007, which is hereby incorporated by reference in its entirety.

Preferably, the pallet of the patient bed is pre-marked with a reference height calibration (RHC) position. It is also preferable to use a center of rotation (COR) mark. The reference height calibration (RHC) preferably comprises preparing a point source (Co57 or Tc99m). The point source is preferably prepared in the same manner as a COR source is prepared.

Preferably, the reference height calibration (RHC) comprises moving the patient bed to a default Z position. The COR bed position is preferably used as the default Z position.

From the default Z position, the height of the patient bed or table is adjusted by an amount $Y_{CT} - Y_{NMScan}$, either manually or automatically via a CAN message to the CT device. For example, based on typical heights as shown in FIG. 2, the table height would preferably be adjusted to the design height by moving the table 170 mm, since $Y_{CT}$ is specified in FIG. 2 as 1030 mm, and $Y_{NMScan}$ is specified in FIG. 2 as 860 mm.

Next, the gamma camera detectors are moved to a default orbit-marking position. The default orbit-marking position is preferably 0 degrees with known detector X and Y positions.

A point source is then placed on the table at a known height. Preferably, the COR bracket can be used to place the point source.

Figure 3:
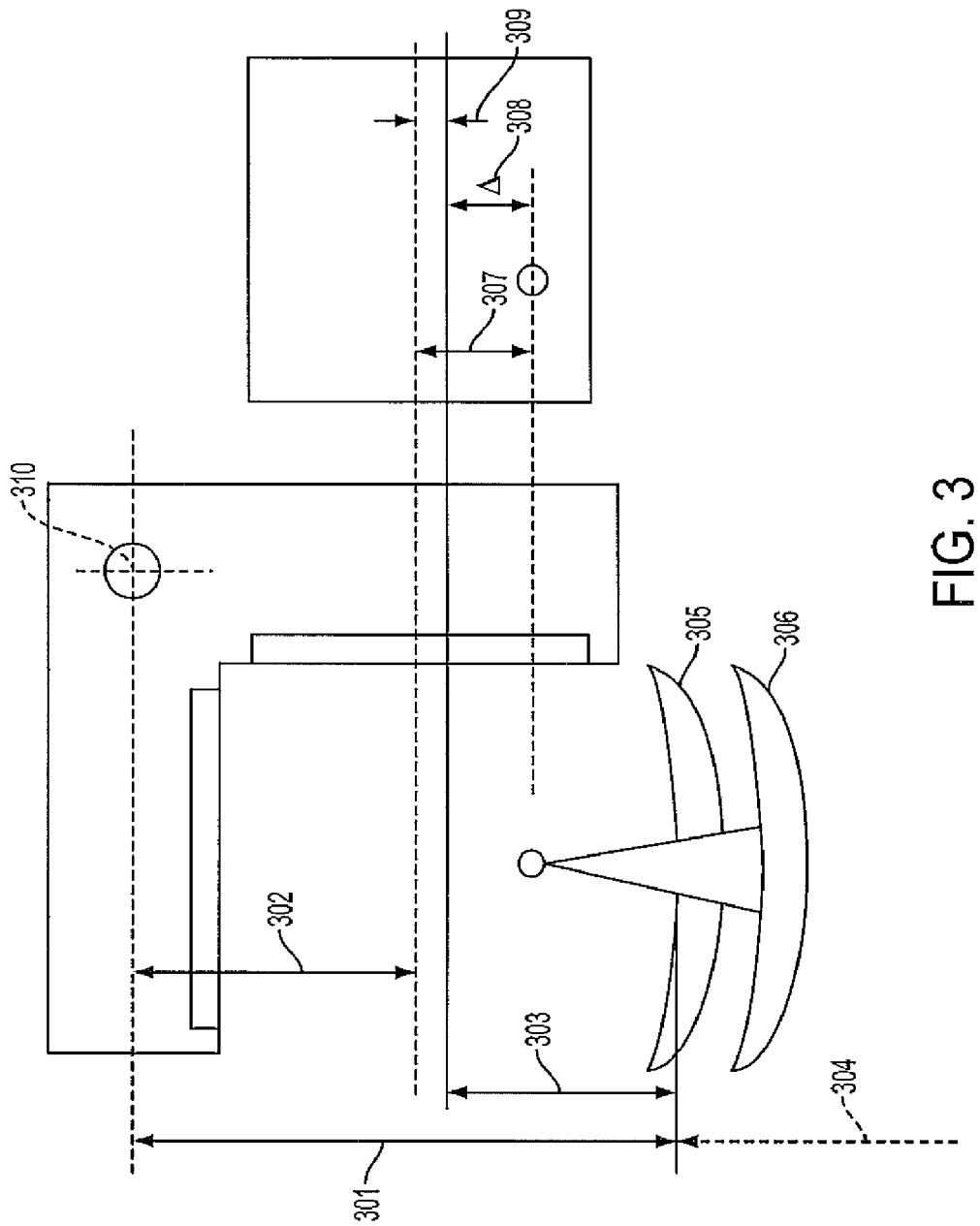
FIG. 3: shows a calculation of height reference error between a SPECT detector and a CT detector in a modular multi-modality imaging system of a type applicable to the present invention.

Next, a static image of the point source is taken with the gamma camera detectors normal to the point source. It is noted that FIG. 3 shows a dual-head gamma camera with detector heads oriented at 90 degrees with respect to each other, and which heads swivel about a pivot point 310. However, the procedure also may be used with a single camera head.

The reference error Δ is then calculated from the acquired image, as described further below. The reference error Δ is then stored for the adjustment of $Y_{NMCenter}$, and updating $Y_{NMScan}$ via either F/W commands or CAN messaging to CT.

As shown in FIG. 3, the height reference error Δ (308) is preferably calculated by formula 2, $$\Delta = Y_{Measured} - Y_{Designed} \quad 2,$$

where $Y_{Measured}$ (307) is the measured distance from the center of the point source image to the center of the FOV of the gamma camera, as obtained from the acquired static image. $Y_{Designed}$ (309) is calculated as:

$$Y_{Designed} = Y_{pvt-bed} - Y_{pvt-cntr} - Y_{Point} \quad 3,$$

where $Y_{pvt-bed}$ (301) is distance between the pivot (310) of the gamma camera and the bed at the default position (306); $Y_{pvt-cntr}$ (302) is the distance between the pivot (310) and the FOV central line; $Y_{point}$ (303) is the height of the calibration bracket supporting the point source. Preferably, $Y_{pvt-bed}$ (301), $Y_{pvt-cntr}$ (302), and $Y_{Point}$ (303) are all known values.

Preferably, to calculate $Y_{Measured}$, the acquired static image is first segmented based on certain threshold criteria, which depend on the activity level of the point source used. Optimal parameters are preferably achieved through experience with COR calibration, and through routine experimentation. The reference error so calculated is then used to adjust the patient bed to design position (305).

Preferably, the RHC procedure is implemented a special mode of the COR calibration, for example, by checking a checkbox on the COR calibration user interface (UI). When the UI is in RHC mode, the system preferably first performs RHC, according to the present invention, then lowers the bed by Δ, and proceeds with the regular COR calibration. The reference error Δ may vary with different collimators, thus preferably the RHC as well as the FOV calibration are all performed per collimator pair.

The RHC is preferably performed at installation. Additionally, it is preferable to perform RHC whenever CT performs re-alignment calibration with the bed which is shared by the NM subsystem. Preferably, RHC does not involve Siemens E.SOFT™ activities for processing needs. It is particularly preferable that a UI display the required table height and in/out table position for NM scans. Preferably, the RHC determines the error in CRL so that the table height is set within the tolerance of the SPECT module for NM scans.

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C §112, sixth paragraph. In particular, the use of "step of" in the claims herein is not intended to invoke the provisions of 35 U.S.C §112, sixth paragraph.

What is claimed is:

1. A method for calibrating height differences between modules in a loosely coupled multi-modality medical imaging system, comprising:

imaging, with a nuclear imaging modality of said system, a point source placed at a known height with respect to a patient bed, wherein said patient bed is located at a known reference level;

calculating a design height using a first known distance between a known location on said nuclear imaging modality and said patient bed at said known reference level, a second known distance between said known location and a central line of a field of view of said nuclear imaging modality, and said known height;

calculating, from said point source image, a measured distance of said point source from a center of said field of view;

calculating a reference error as a difference between said measured distance and said design height; and storing said reference error to adjust the height of said patient bed during a multi-modality imaging procedure.

2. The method according to claim 1, wherein one of the modules is a computed tomography (CT) scanner, and the steps are repeated whenever the CT scanner performs re-alignment calibration with the bed.

3. The method according to claim 1, wherein said reference error is further used to adjust a height registration parameter between said modules.

4. The method according to claim 1, wherein said nuclear imaging modality is a dual-head gamma camera.

5. The method according to claim 4, wherein said heads are oriented at 90 degrees with respect to each other during said imaging of said point source.

6. The method according to claim 4, wherein said known location on said dual-head gamma camera is a pivot point for swiveling of the heads of said gamma camera.

7. The method according to claim 1, wherein said design height is determined by subtracting said second known distance and said known height from said first known distance.

* * * * *